United States Patent [19]

Powell et al.

[11] Patent Number: 5,113,013
[45] Date of Patent: May 12, 1992

[54] PROCESS FOR PREPARING FLUORINE-CONTAINING ORGANIC COMPOUNDS

[75] Inventors: Richard L. Powell; Charles A. Heaton, both of Cheshire, England

[73] Assignee: Imperial Chemical Industries PLC, London, England

[21] Appl. No.: 515,509

[22] Filed: Apr. 26, 1990

[30] Foreign Application Priority Data

Apr. 26, 1989 [GB] United Kingdom ............... 8909574

[51] Int. Cl.$^5$ .............................................. C07C 63/04
[52] U.S. Cl. ................................... 562/493; 568/933; 568/936; 570/123
[58] Field of Search ............... 562/493; 568/933, 936; 570/123

[56] References Cited

FOREIGN PATENT DOCUMENTS 1010240 11/1961 United Kingdom .

Primary Examiner—Paul J. Killos
Attorney, Agent, or Firm—Cushman, Darby & Cushman

[57] ABSTRACT

A method for the preparation of a fluorine-containing organic compound which comprises reacting a sulphonyl halide of the formula:

$$R_fSO_2X$$

where Rf represents a fluorinated organic radical and X represents a halogen atom, with a reactive organic halide in the presence of a metal known to complex with fluorinated organic radicals.

5 Claims, No Drawings

PROCESS FOR PREPARING FLUORINE-CONTAINING ORGANIC COMPOUNDS

This invention relates to a chemical process and more particularly to a process for the preparation of fluorine-containing organic compounds.

According to the invention there is provided a method for the preparation of a fluorine-containing organic compound which comprises reacting a sulphonyl halide of the formula:

$$R_fSO_2X \qquad (1)$$

wherein $R_f$ represents a fluorinated organic radical and X represents a halogen atom, with a reactive organic halide in the presence of a metal known to complex with fluorinated organic radicals.

Sulphonyl halides of Formula 1 which may be used in the method of the invention particularly include chlorides but other halides, for example fluorides, may be used.

The fluorinated organic radical $R_f$ in the sulphonyl halides may be a perfluorinated or partially fluorinated organic radical. Typical radicals include perfluoroalkyl and perfluoroaryl (for example perfluorophenyl) radicals and radicals of the formula:

$$QCF_2-$$

wherein Q represents an alkyl radical which may contain one or more fluorine atoms. As an example of a fluorinated organic radical, there may be mentioned the trifluoromethyl radical.

Sulphonyl fluorides of Formula 1 wherein $R_f$ is a perfluoroalkyl radical may be obtained by, for example, electrochemical fluorination of the corresponding aliphatic sulphonyl chlorides. The fluorides can then be converted to chlorides or other halides by conventional methods.

Reactive organic halides which may be used in the method of the invention particularly include activated aromatic halides.

Activated aromatic halides include aromatic compounds, which may be carbocyclic or heterocyclic, containing at least one halogen atom, especially chlorine, and at least one electron withdrawing group for example nitro, cyano, carboxyalkyl, carbamoyl, trifluoromethyl and the like. Useful activated aromatic halides include activated halogenobenzenes, for example 2-nitrochlorobenzene, 4-nitrochlorobenzene, 2,4-dinitrochlorobenzene, 2-nitrobromobenzene, 2,6-dinitro-4-(trifluoromethyl) chlorobenzene and the like.

Metals known to complex with fluorinated organic radicals include cadmium, zinc, mercury, silver and, especially, copper. The copper or other metal employed in the method of the invention is suitably in finely divided form, for example copper bronze.

In carrying out the method of the invention, the sulphonyl halide and reactive organic halide may be reacted in the presence of the metal in dipolar aprotic solvents, for example, dimethylformamide, dimethylacetamide or N-methylpyrrolidone, at elevated temperatures. In general, the reaction proceeds at a satisfactory rate at room temperature but lower temperatures, for example −20° C., or higher temperatures, for example 120° to 140° C., may be used if desired.

The presence of a complexing agent such as 2,2'-bipyridyl in the reaction mixtures can have a beneficial effect.

The reaction generally proceeds in a satisfactory manner using about one mole of sulphonyl halide per equivalent of replaceable halogen in the reactive organic halide but it is sometimes advantageous to use an excess of sulphonyl halide.

At the end of the reaction, the desired product may be isolated from any unchanged starting materials using conventional separation techniques.

The method of the invention provides an efficient means of replacing halogen atoms in reactive organic halides by fluorinated organic radicals, for example perfluoroalkyl radicals, the products being useful as chemical intermediates in the production of pharmaceuticals, agrochemicals and the like.

The invention is illustrated but not limited by the following Examples.

EXAMPLE 1

Copper bronze (30.0 g), 2,2'-bipyridyl (3.0 g) and N,N-dimethylacetamide (DMAC) (200 cm³) were placed in a 1 liter 3-necked flask and nitrogen was allowed to purge the system.

$CF_3SO_2Cl$, (40 g in DMAC 50 cm³) was then added dropwise to the stirring copper solution. This was followed by a further 25 cm³ of DMAC as a wash. The mixture was stirred for ½hr at room temperature to yield a dark green solution containing some metallic copper. 4-trifluoromethyl-2,6-dinitrochlorobenzene (15.9 g in 50 cm³ DMAC) was then added dropwise to the stirring solution. This was followed by a further 50 cm³ of DMAC as a wash. The solution was then stirred for 1 hr at room temperature, yielding a green brown solution containing a black solid.

The solution was then heated to 105° C. for 5 hrs. The solution was monitored by GC and was then allowed to cool slowly to room temperature leaving a dark green/brown solution containing a black solid.

The solution was then filtered to remove the black solid. Diethyl ether (200 cm³) was added and the mixture shaken. This was followed by water (1000 cm³) which caused a brown solid to precipitate which created a strong exotherm and some effervenscence. Filtration was attempted without success. A further 700 ml ether was added followed by 500 cm³ of distilled water. The mixture was then shaken and allowed to stand for ½ hr. Separation did not occur. The mixture was then filtered successfully with the use of 'Hyflo supercel filter aid', removing a brown solid which turned green upon exposure to air. After filtration, separation was achieved giving a brown ether layer and a green aqueous layer.

The aqueous layer was further extracted using diethyl ether (3×100 cm³). The ether extracts were then combined and washed with water (5×200cm³). The extracts were dried over $MgSO_4$ before the removal of ether by distillation. This resulted in the formation of a dark brown solid/liquid (12 g).

A sample was (7.3 g) of the product was redissolved in diethyl ether and then recrystallised. The crystals were then removed by filtration and washed with Ice-cold diethyl ether, to yield very pale yellow crystals (1.47 g) m.p. 88.0°-88.7° C. A further 0.5 g of crystals was obtained from the ether washings.

The sample obtained from recrystallisation in diethyl ether was found to be 99.5% pure by GC analysis, Crystals obtained from the etheric wash were found to be 99.6% pure by GC analysis. A further sample was obtained from the ether washings (0.26 g) those crystals were found to be 99.2% pure by GC analysis.

The following Table gives further Examples of the method of the invention.

| EXAMPLE | RfSO$_2$X | ORGANIC HALIDE | COPPER | SOLVENT | TEMP (°C.) | TIME (h) | PRODUCT |
|---|---|---|---|---|---|---|---|
| 2 | C$_4$F$_9$SO$_2$Cl 3.5 g | 2,4-dinitrochlorobenzene 1.2 g | 1.5 g | DMF 30 ml | 100 130 150 160 180 | 0.5 1.0 2.0 7.0 7.5 | 2,4-dinitroperfluorobutyl benzene |
| 3 | C$_6$F$_{13}$SO$_2$Cl 4.8 g | 2,6-dinitro-4-trifluoro methyl chlorobenzene 1.2 g | 1.5 g | DMF 30 ml | 130 180 | 0.5 12 | 2,5-dinitro-4-trifluoromethyl perfluorohexyl benzene |
| 4 | C$_8$F$_{17}$SO$_2$F 2 g | 2,6-dinitro-4-trifluoro methyl chlorobenzene 1.08 g | 1.02 g | DMAC 30 ml | 130 | 5 | 2,6-dinitro-4-trifluoromethyl perfluoro-octyl benzene |
| 5 | C$_6$F$_5$SO$_2$Cl 1.57 g | 2,6-dinitro-4-trifluoro methyl chlorobenzene 1.6 g | 1.5 g | DMAC 30 ml | 140 | 12.5 | 2,6-dinitro-4-trifluoromethyl perfluorophenyl benzene |
| 6 | CF$_3$SO$_2$Cl 8 g | 2-nitrobromobenzene 2.42 g | 1.5 g | DMF 30 ml | 100 140 | 1 5 | 2-nitrotrifluoromethylbenzene |
| 7 | CF$_3$SO$_2$Cl 8 g | 2-nitroiodobenzene 2.99 g | 1.5 g | DMF 30 ml | 100 140 | 1 5 | 2-nitrotrifluoromethylbenzene |
| 8 | CF$_3$SO$_2$Cl 2 g | 4-iodobenzoyl chloride 0.8 g | 1.5 g | DMF 30 ml | 25 100 | 0.5 4 | 4-trifluoromethylbenzoic acid |

We claim:

1. A method for the preparation of a fluorine-containing organic compound which comprises reacting
   (a) a sulphonyl halide of the formula Rf SO$_2$X wherein Rf represents a perfluoroalkyl group or a perfluoroaryl group or a group of the formula QCF$_2$ where Q is an alkyl radical optionally containing one or more fluorine atoms and X is a halogen atom with
   (b) a reactive organic halide which is an activated aromatic halide containing at least one halogen atom and at least one electron withdrawing group in the presence of a metal known to complex with fluorinated organic radicals selected from the group consisting of cadmium, zinc, mercury, silver and copper.

2. A method according to claim 1 wherein the sulphonyl halide is a chloride or fluoride.

3. A method according to claim 1 wherein Rf represents a perfluoroalkyl or perfluoroaryl radical.

4. A method according to claim 1, wherein the reactive organic halide is an aromatic compound containing at least one halogen atom and at least one electron-withdrawing group.

5. A method according to claim 1, wherein the metal is copper.

* * * * *